United States Patent
Niazi et al.

(12)
(10) Patent No.: US 6,312,735 B1
(45) Date of Patent: Nov. 6, 2001

(54) METHOD FOR INSTANTANEOUS REMOVAL OF WARTS AND MOLES

(76) Inventors: Sarfaraz K. Niazi, 20 Riverside Dr.; Riaz K. Niazi, 733 Elder La., both of Deerfield, IL (US) 60015

( * ) Notice: Subject to any disclaimer, the term of this patent is extended or adjusted under 35 U.S.C. 154(b) by 0 days.

(21) Appl. No.: 09/681,176

(22) Filed: Feb. 9, 2001

(51) Int. Cl.[7] ............... A61K 6/00; A61K 7/00; A61K 33/08; A01N 59/06
(52) U.S. Cl. ............ 424/694; 424/430; 424/401; 132/76.4
(58) Field of Search .................. 424/430, 401, 424/694; 606/131; 132/76.4

(56) References Cited

U.S. PATENT DOCUMENTS 5,997,549 * 12/1999 Sauceda et al. ............. 606/131

OTHER PUBLICATIONS

Derwent Abstract 1989–300878 of Liu, CN 8805705, published Nov. 9, 1988.*
Woodruff, John. "Adding the Natural Touch to Cosmetics," Manufacturing Chemist, Dec. 1998, vol. 69, issue 12, p. 18.*
Martha Tilaar Salon & Spa Bali–Sari Ayu Skin Care Product for Special Treatment, product brochure, 2000.*
Liao et al., "Contact leukomelanosis induced by the leaves of Piper betle L. (Pieraceae): A clinical and histopathologic survey," Journal of the American Academy of Dermatology, Apr. 1999, vol. 40, issue 4, pp. 583–589.*

* cited by examiner

Primary Examiner—Michael G. Hartley
Assistant Examiner—Michael A. Willis

(57) ABSTRACT

Disclosed here is a method for the removal of all types of human and animal skin warts using a technique of cauterization wherein slaked lime is applied to wart and then the surface of wart is scratched by using the stem of betel leaf.

5 Claims, No Drawings

METHOD FOR INSTANTANEOUS REMOVAL OF WARTS AND MOLES

DETAILED DESCRIPTION

Warts are a widespread medical problem that cause pain and discomfort, and may lead to complications if untreated or improperly treated. Warts are benign growths of the skin caused by a virus that involves the epidermis. Five different types of warts are classified by their clinical presentation: (1) Verrucae vulgares are common warts that display hyperkeratosis and may occur anywhere except the genital and mucous membranes and plantar surfaces (soles of the feet); (2) Verrucae planae are flat warts that usually occur on the face, trunk and extremities; (3) Verrucae plantares are warts that occur only on the soles of the feet; (4) Condylomata acuminata are venereal warts that occur on the genitals and mucous membranes; (5) premalignant warts (Epidermoldysplasia verruciformis) usually occur on the hands and feet and are rare in occurrence. Currently, there are no completely successful, treatments for warts. Current treatments of verrucae involve physical destruction of the infected cells. Choice of treatment depends on the location, size, number, and type of wart, age and co-operation of the patient. No single treatment modality is uniformly effective or directly antiviral. Antiwart treatments include cryotherapy with liquid nitrogen, caustics and acids such as salicylic acid, lactic acid and trichloroacetic acid, which destroy and peel off infected skin. Retinoic acid has been used topically to treat flat warts. Cantharidin is an extract of the green blister beetle that leads to blistering and focal destruction of the epidermis. Induction of allergic contact dermatitis with dinitrochlorobenzene (DNCB) produces local inflammation to warts on which this chemical has been applied. Chemotherapeutic agents also employed for venereal warts include topically applied podophyllin resin, which is more effective on mucosal surfaces. It is contraindicated in pregnancy and the potency of podophyllin preparations may be highly variable. Purified podophyllotoxin is available having activity that is reproducible in vitro Application of 5-fluorouracil is sometimes used to treat flat warts and Condylomata acuminata. Intralesional bleomycin has also been used but may cause extensive tissue necrosis. Curettage, electrodesiccation, $CO_2$, and lasers are also used to treat warts. These treatment modalities are often painful and may require anesthesia and cause scarring. A new immunomodulator, Imiquimod has recently been used to topically treat genital and perianal warts. Salicylic acid in a topical composition is available for the treatment of warts. In this form, salicylic acid is a keratolytic agent that softens the hyperkeratotic areas by dissolving the intra-cellular matrix and enhancing shedding of scales. This composition is nonspecific, being also used for the treatment of psoriasis and other hyperkeratotic disorders. Unfortunately, application of salicylic acid is not always effective for wart resolution. Many patients with warts become frustrated while using salicylic acid because it is ineffective, forcing those patients to seek medical consultation. This may result in applying physical or surgical agents to alleviate patient distress. Because no effective extemporaneous keratolytic treatment to remove warts without appreciable side effects is yet available, other modalities are needed. In this invention we have used and extemporaneous application of slaked lime and betel leaf stem to instantly remove warts from human skin surface.

Slaked lime contains at least 95% calcium hydroxide ($CaH_2O_2$), prepared commercially by hydration of lime (W. L. Faith et al., Industrial Chemicals. John Wiley & Sons, $3^{rd}$ Ed., 1965, New York, N.Y.). It is crystalline or soft, odorless, granules of powder with slightly bitter alkaline taste. It readily absorbs carbon dioxide from air forming calcium carbonate; upon igniting it loses water forming calcium oxide (CaO). It is slightly soluble in water, soluble in glycerol, sugar or ammonium chloride solutions. The pH of saturated solution is 12.4. LD50 orally in rats is 7.34 g/kg (The Merck Index $12^{th}$ Ed., Merck & Co., Whitehouse Station, N.J.).

Betel leaf (Piper betle L. (Piperaceae) is also called Ju Jiang Ye in Chinese medicine. One of the most popular uses of betel leaf is in the composition called, "betel," which is a compound of natural substances chewed for its psycho-stimulating effects. Betel is composed of the nut of the areca palm (Areca catechu), the leaf of the betel pepper (Piper betle), and lime (calcium hydroxide). Approximately 300 million persons chew betel regularly throughout the western Pacific basin and south Asia. Only three drugs (nicotine, ethanol, and caffeine) are consumed more widely than betel. When betel is chewed, it produces mild psychoactive and cholinergic effects. There is copious production of blood-red saliva that can stain oral structures. After years of chewing, the teeth may become red-brown to nearly black. Betel use is associated with oral leukoplakia, submucous fibrosis, and squamous cell carcinoma. Use of betel is discouraged in Western countries because of its alleged carcinogenic and perceived dysesthetic properties; nevertheless, betel is widely available in the West. (Norton S A, Betel: consumption and consequences: J Am Acad Dermatol January;38(1):81–8, 1998). It contains many phenols including anti-nitrosating phenolic compounds (Nagabhushan, M., et al., Hydroxychavicol: a new anti-nitrosating phenolic compound from betel leaf, Mutagenesis, May;4(3):200–4, 1989). The anecdotal use of the prescribed combination of the components of betel exists because of a balance of chemical activity brought about mutually by the components. Betel leaf has antiviral properties and its component appear to be better extracted when combined with slaked lime.

This invention describes a technique for the removal of warts by applying slaked lime to wart and scratching the wart surface using the stem of betel leaf. The possibility exists that betel leaf acts as an antiviral agent that invades the infected epidermal cells and kills the virus within the cells. It is also possible that the alkalinity of slaked lime facilitates the entry of betel leaf components into the infected cell by disturbing the intercellular matrix of the wart, dissolving the protein and thus changing the physical-chemical properties of infected cell membranes. Entry of the betel leaf components and/or the slaked lime then produces a more effective cauterization of wart and a more esthetically acceptable scarring afterwards. The mode of treatment itself may have significant impact on the efficacy of combination. The historical use of slaked lime with betel leaf for chewing purpose indicates an anecdotal interaction between the two components. Used in this invention is the stem of betel leaf, the small stud, which is removed from betel leaf prior to using it. The methodology of application involves first applying slaked lime to wart in sufficient quantity to cover it entirely and the surrounding area and then scratching the wart with the stub or stem of betel leaf first gently and then aggressively over the surface of wart. In most instances, the wart begins to soften and disintegrate within a few minutes of application. Repeated applications may be necessary for chronic warts and warts covering larger surface area of skin.

The system of the betel leaf can be used in combination with other mechanical devices or chemicals, or in conjunction with or applied concurrently with other modalities, to remove moles and warts.

We claim:

1. A method of removing warts and moles comprising application of a composition comprising slaked lime to the surface of a wart or mole followed by rupture of the surface of the wart with the stub of the stem of betel leaf.

2. The method of claim 1 wherein the slaked lime is a form of calcium hydroxide, $Ca(OH)_2$, obtained by the addition of water to calcium oxide or lime to produce a solution or slurry of pH 12.4.

3. The method of claim 1 wherein the betel leaf is Piper betel.

4. The method of claim 1, wherein the surface of the wart or mole is further aggravated with an implement selected among the group consisting of a mechanical device and a sharp object.

5. The method of claim 1, wherein the wart or mole is any type of external wart or mole on a human or animal.

* * * * *